US010548505B2

(12) United States Patent
Rothgang et al.

(10) Patent No.: US 10,548,505 B2
(45) Date of Patent: Feb. 4, 2020

(54) SYSTEM AND METHOD FOR REAL-TIME MRI-GUIDED OBJECT NAVIGATION

(71) Applicants: Siemens Healthcare GmbH, Erlangen (DE); The Johns Hopkins University, Baltimore, MD (US)

(72) Inventors: Eva Rothgang, Nürnberg (DE); Arne Hengerer, Möhrendorf (DE); Lars Lauer, Neunkirchen (DE); Jan Fritz, Baltimore, MD (US); Paul Bottomley, Columbia, MD (US); Wesley David Gilson, Northbeach, MD (US); Robert Grimm, Nürnberg (DE)

(73) Assignees: Siemens Healthcare GmbH, Erlangen (DE); The Johns Hopkins University, Baltimore, MD (US)

( * ) Notice: Subject to any disclaimer, the term of this patent is extended or adjusted under 35 U.S.C. 154(b) by 996 days.

(21) Appl. No.: 15/070,116

(22) Filed: Mar. 15, 2016

(65) Prior Publication Data

US 2017/0269174 A1    Sep. 21, 2017

(51) Int. Cl.
*A61B 5/055* (2006.01)

(52) U.S. Cl.
CPC ................... *A61B 5/055* (2013.01)

(58) Field of Classification Search
CPC ...................................................... A61B 5/055
See application file for complete search history.

(56) References Cited

U.S. PATENT DOCUMENTS

| 10,004,462 | B2 * | 6/2018 | Ernst | .................... A61B 6/5205 |
| 2013/0114872 | A1 | 5/2013 | Chen et al. | |
| 2015/0285889 | A1 * | 10/2015 | Chen | ...................... A61B 5/055 |
| | | | | 324/309 |

OTHER PUBLICATIONS

Shashank S. Hegde et al., Acceleration and Motion-Correction Techniques for High-Resolution Intravascular MRI, Magnetic Resonance in Medicine 2015(2); 74:452-461.
Michael Lustig et al., Compressed Sensing MRI, IEEE Signal Processing Magazine (72), Mar. 2008, pp. 72-82.
Jonathan S. Lewin et al., Needle Localization in MR-Guided Biopsy and Aspiration: Effects of Field Strength, Sequence Design, and Magnetic Field Orientation, American Journal of Roentgenology, 166(6), 1337-1345 (1996).

(Continued)

*Primary Examiner* — Rochelle D Turchen (57) ABSTRACT

A magnetic resonance method and system are provided for magnetic resonance (MR) image-guided insertion of an object into a biological tissue along a predetermined trajectory. The trajectory provides a path between a starting point and a target site within the tissue. Sufficiently high resolution images can be generated in real time to precisely guide the needle placement. A compressed sensing approach is used to generate the images based on minimization of a cost function, where the cost function is based on the predetermined needle path, artifact effects associated with the needle, the negligible changes in the images away from the trajectory, and the limited differences between successive images. The improved combination of spatial and temporal resolution facilitates an insertion procedure that can be continuously adjusted to accurately follow a predetermined trajectory in the tissue, without interruptions to obtain verification images.

20 Claims, 3 Drawing Sheets

(56) References Cited

OTHER PUBLICATIONS

Jeffrey L. Duerk et al., Application of Keyhole Imaging to Interventional MRI: A Simulation Study to Predict Sequence Requirements, Journal of Magnetic Resonance Imaging 6(6), 918-924 (1996).

* cited by examiner

FIG. 3 ures. Such MRI techniques can provide near-continuous imaging, e.g., at several frames per second, while the needle is advanced within a subject. However, obtaining highly-resolved verification image datasets in- between small needle advancements is needed to verify the exact needle position before it is advanced further. These higher-resolution verification datasets often have an acquisition time of 20 seconds or more, and thus slow down the needle positioning procedure. The workflow interruptions needed to accurately verify needle positions during the advancement process slow down the overall procedure and impede a continuous insertion process.

SYSTEM AND METHOD FOR REAL-TIME MRI-GUIDED OBJECT NAVIGATION

STATEMENT REGARDING FEDERALLY SPONSORED RESEARCH

The present invention was made with government support under National Institutes of Health Grant No. NIH R01 EB007829. The government has certain rights in the invention.

FIELD OF THE DISCLOSURE

The present disclosure relates to a system and method for tracking a moving needle or other object while it is being inserted into biological tissue, using improved magnetic resonance imaging (MRI) techniques that can provide sufficiently high resolution images in real time to precisely guide the needle placement. The MRI techniques employ a compressed sensing approach that takes advantage of the pre-determined needle path, known artifact effects associated with the needle, and the unchanging nature of images away from the needle path to provide images having improved resolution in real time, thereby avoiding the need to interrupt the needle advancement periodically to obtain slow high- resolution verification images.

BACKGROUND INFORMATION

Image-guided or image-assisted) procedures are medical procedures that require precise insertion or placement of an object within a subject. Such procedures (also referred to as 'interventions') are often percutaneous interventions, and the inserted object can be a medical device or instrument such as, for example, a catheter, an electrode, a needle, or the like. Percutaneous interventions can be used for biopsies, thermal ablations, infiltrations, etc. of a target structure. Imaging techniques for such procedures can include, e.g., ultrasound, x-ray, or magnetic resonance (MR) imaging.

For real-time MR-guided needle placement (e.g. biopsy, infiltration, placement of a thermal applicator such as a radio frequency (RF) ablation needle), it is essential to continuously monitor the needle, surrounding sensitive structures and the target structure. Thus, fast image acquisition is needed, e.g., at a rate of several frames per second (fps). A selection of different soft-tissue contrasts is also desirable. For example, some tumors can only be seen in a highly spin-spin relaxation time-weighted (T2-weighted) image. A high spatial resolution is advantageous e.g., when addressing small target structures such as small lesions and the like. However, T2-weighted imaging typically requires a long repetition time TR, and acquisition times for a single frame/image can be on the order of several seconds. Some 'fast' imaging methods, such as turbo spin-echo (TSE) sequences, also have acquisition times that are typically more than a second for a single image. Further, there is generally a trade-off between acquisition time and spatial resolution, with higher image resolutions requiring longer acquisition times. A summary of imaging requirements for interventional MRI procedures, and some proposed approaches to improve speed and efficiency of image acquisition for such procedures, is provided, e.g., in J. L. Duerk et al., *Journal of Magnetic Resonance Imaging* 6(6), 918-924 (1996), which is incorporated herein by reference in its entirety.

Typically, fast imaging sequences such as spin-lattice relaxation time-weighted (T1-weighted) gradient-recalled echo (GRE) or FISP (fast imaging with steady state precession), e.g., True-FISP (a balanced FISP technique in which the magnetic gradient moments sum to zero for each TR), are used for real-time MM-guided needle placement procedures. Such MRI techniques can provide near-continuous imaging, e.g., at several frames per second, while the needle is advanced within a subject. However, obtaining highly-resolved verification image datasets in- between small needle advancements is needed to verify the exact needle position before it is advanced further. These higher-resolution verification datasets often have an acquisition time of 20 seconds or more, and thus slow down the needle positioning procedure. The workflow interruptions needed to accurately verify needle positions during the advancement process slow down the overall procedure and impede a continuous insertion process.

Accordingly, it would be desirable to have a system and method for real-time MRI suitable for guiding the insertion or placement of medical devices (such as needles or catheters) within a subject, which addresses some of the shortcomings described above.

SUMMARY OF EXEMPLARY EMBODIMENTS

Exemplary embodiments of the present disclosure can provide magnetic resonance imaging systems and methods for real-time MRI of an object (such as a needle) while it is being inserted into biological tissue, using improved MRI techniques that can provide sufficiently high resolution images in real time to precisely guide the needle placement. The MRI techniques employ a compressed sensing approach that takes advantage of a pre-determined object path, known artifact effects associated with the object, the unchanging nature of images away from the object path, and the limited differences between successive images, where these factors are expressed as a cost function that can be minimized using the compressed sensing approach. The improvements in combined spatial and temporal resolution, as compared to conventional imaging techniques, facilitate an insertion procedure that can be continuously adjusted to accurately follow a predetermined trajectory in the tissue.

Certain embodiments of the present disclosure can provide a method for real-time magnetic resonance imaging to facilitate insertion of an object within a biological tissue along a predetermined path and/or into a predetermined target region within the tissue. Further embodiments provide an MRI system that is configured to perform or facilitate such method. Such MRI system can be configured to generate sequences of gradient and RF pulses and display generated images in substantially real time for improved MRI guidance of certain procedures such as interventions and electrode placements. The MRI method and system include obtaining and processing image data using compressed sensing techniques, which allows both the temporal nature of the procedure and qualitative differences in the signal changes in the planned object path/trajectory and in regions away from this path to generate a series of images of the object and surrounding biological tissue in substantially real time, at a sufficiently high image resolution to facilitate real-time guidance of advancement/placement of the object in the tissue.

In embodiments of the disclosure, the MR system and method can generate high-resolution images, e.g., having an in-plane spatial resolution between about 0.5 mm to 2 mm in the region that includes the needle or object/instrument path. In certain embodiments, higher or lower spatial resolutions may be generated. Such images can be generated at frame rates, e.g., that are about 0.5 to 15 frames per second (fps). In further embodiments, higher or lower temporal frame rates may be used.

Prior to an insertion or placement procedure, a needle/object trajectory can be determined using a high-resolution MM technique such as, e.g., a turbo spin echo (TSE) sequence, a gradient recalled echo (GRE) sequence, or a fast imaging with steady-state precession and balanced gradients (true-FISP) sequence, to generate an image of the region of the subject that contains the internal target site and desired insertion path of the object (e.g. needle). In some embodiments, the spatial trajectory for the insertion procedure can be determined as a substantially straight line connecting an insertion point on the tissue surface and a target site within the tissue. In further embodiments, the trajectory may be curved or have other properties based on, e.g., the presence of other anatomical structures or objects within the tissue.

The planning image data can be obtained by, stored in memory of, and displayed by the MRI system. The trajectory can then be determined either automatically (e.g. as a straight line) or optionally it can be determined interactively by a user, e.g., by manipulating the displayed planning image, using any appropriate input method to identify the endpoints of the path (e.g. the insertion point and the target site). The MRI system can be configured to store three dimensions data defining the planned trajectory in a memory arrangement.

For a particular MR imaging protocol and set of parameters (e.g. main field strength, echo times, etc.), together with the size/material and approximate orientation of the object to be inserted, an expected or predicted imaging artifact size and shape can be predicted for various imaging plane orientations using known data and MR techniques. This information can also be stored and processed by the MRI system, and utilized in the imaging procedures described herein to more accurately track the position of the needle during an intervention or similar procedure.

In some embodiments, an approximate region of interest (ROI) that includes a volume of tissue surrounding and close to the predetermined trajectory can be identified. The ROI can be, e.g., a substantially cylindrical volume having its axis along the trajectory. For example, the ROI can typically encompass or include a volume within a radius of about 1-2 cm around the preplanned trajectory. Other shapes and/or sizes for the ROI can be defined in further embodiments, for example, based on the shape of the needle, the shape of the desired trajectory, and characteristics of the nearby tissue. Reconstruction of images of the volume lying outside of the ROI can be bypassed or performed at a reduced resolution, using known techniques such as data masking, to further reduce image processing time, e.g., during a guided procedure.

Embodiments of the present disclosure include using compressed sensing (CS) techniques to facilitate reconstruction of images based on a low sampling rate of the raw image data, e.g. a rate that is below the Nyquist sampling rate. The signal reconstruction can often be well-approximated by determining only the limited set of large transform coefficients in the sparsity space. Any known CS techniques that are appropriate for reconstructing MRI signals and generate images therefrom can be used in embodiments of the disclosure.

In some embodiments, undersampled images at different time points can be combined to generate a single 'composite' or 'joint' image, to decrease potential artifacts and reduce the effective degree of undersampling when displaying or analyzing the image.

Embodiments of the present disclosure can use CS techniques with a compressed sensing cost function $f(x_t)$ having the following form:

$$f(x_t) = \underbrace{\frac{1}{2}\|Ax_t - y\|_2^2}_{\text{Match measured data}} + \underbrace{\lambda_1\|x_t - (x_{ref} + \hat{x}_{Needle,t})\|_1}_{\text{Similar to predicted image}} + \underbrace{\lambda_2\|x_t - x_{t-1}\|_1}_{\text{Similar to previous frame}} \qquad (1)$$

In this equation, $x_t$ is the current image being computed at time t, A is the MRI sampling operator, y is the measured (raw) k-space data, $x_{ref}$ represents the predicted image without the presence of needle artifacts $\hat{x}_{Needle,t}$ represents a predicted needle artifact, $x_{t-1}$ is the previous image that was computed at time t-1, and $\lambda_1$ and $\lambda_2$ are weighting coefficients. In some embodiments, one or both of the constants $\lambda_1$ and $\lambda_2$ can each be selected to be close to 1, e.g., between about 0.5 and 1.5 to provide a balanced effect of the previous frame data and/or the predicted image data with respect to the actual image data when generating each successive image frame. In further embodiments, one of the weighting coefficients $\lambda_1$ or $\lambda_2$ can be small (e.g., less than about 0.5) or even set to zero, to reduce or eliminate the effect of the corresponding weighted term in the CS cost function.

Each image in the series of MR images can be determined by minimizing the cost function $f(x_t)$ shown in Eq. (1), e.g., using iterative computational techniques known in the art. In this manner, raw MR image data can be used with this cost function to generate real-time high-resolution images of at least the ROI around the predetermined trajectory.

The sparsity condition that facilitates CS techniques can be provided by the latter two terms on the right in Eq. (1), where the actual calculated image will have a sparse difference when compared to the predicted image and/or to the previous image obtained in the previous frame, respectively. In certain embodiments, a FISP sequence can be used to obtain the image data, e.g., a balanced FISP (True-FISP) technique. For example, the phase-encoding gradient steps in a Cartesian FISP data acquisition would be randomly under-sampled except for a fully-sampled region near the origin of k-space which would be fully sampled.

In further embodiments of the disclosure, a spiral or radial k-space sampling sequence can be used to obtain the image data. The angular projections of such spiral or radial sequence (as compared to, e.g., a conventional Cartesian sampling approach) can be randomly under-sampled and lead to, e.g., a reduction in image data acquisition time by a factor of 2 to 10 as compared to a comparable fully-sampled sequence.

An exemplary method in accordance with embodiments of the disclosure can include obtaining a high-resolution "planning" image of the portion of the subject to be treated, and determination of a set of spatial coordinates describing the desired trajectory based on the starting/insertion point and target site for the MRI-guided procedure. The trajectory can optionally be determined with additional user input, e.g., if the trajectory varies from a straight line connecting the insertion point and target site.

The image-guided procedure can then continue by inserting a needle or other object into the subject at the insertion point, where the direction of the needle is substantially aligned with the predetermined trajectory. A series of substantially real-time images of the subject in the region of the procedure can then be obtained as described herein using a compressed sensing technique, and displayed on a display or monitor connected to the MRI system. A graphical representation of the predetermined trajectory can also be generated and superimposed on the MR images of the subject together with the needle artifact that indicates the location of the needle within the subject.

The user can continue to advance the needle/object along the predetermined trajectory based on the displayed MR images. For example, the user can continuously adjust the angle and/or direction of the needle as it is advanced based on the displayed real-time images, such that the insertion procedure proceeds substantially along the predetermined trajectory. The displayed images can optionally be manipulated by user input such that a plurality of viewing angles can be shown, either simultaneously or sequentially, to facilitate directional adjustments to the needle advancement.

Advancement of the needle/object within the subject and generation of MR images of the region around the trajectory can be continued until the object reaches the target site or the procedure is stopped for some other reason. In this manner, the systems and methods described herein can provide accurate real-time imaging during the guided procedure so the insertion follows the predetermined trajectory to the target site.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

While the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present invention as defined by the appended claims.

DETAILED DESCRIPTION OF EXEMPLARY EMBODIMENTS

The present disclosure describes systems and methods for MM-based tracking of a moving needle or other object while it is being inserted into biological tissue (e.g., a percutaneous procedure), using improved MRI techniques that can provide sufficiently high resolution images in real time to precisely guide the needle advancement and placement. The MRI techniques employ a compressed sensing approach that takes advantage of the pre-determined needle path, known artifact effects associated with the needle, and the unchanging nature of images away from the needle path to provide images having improved resolution in real time, thereby avoiding the need to interrupt the needle advancement periodically to obtain slow high-resolution verification images.

Figure 1:
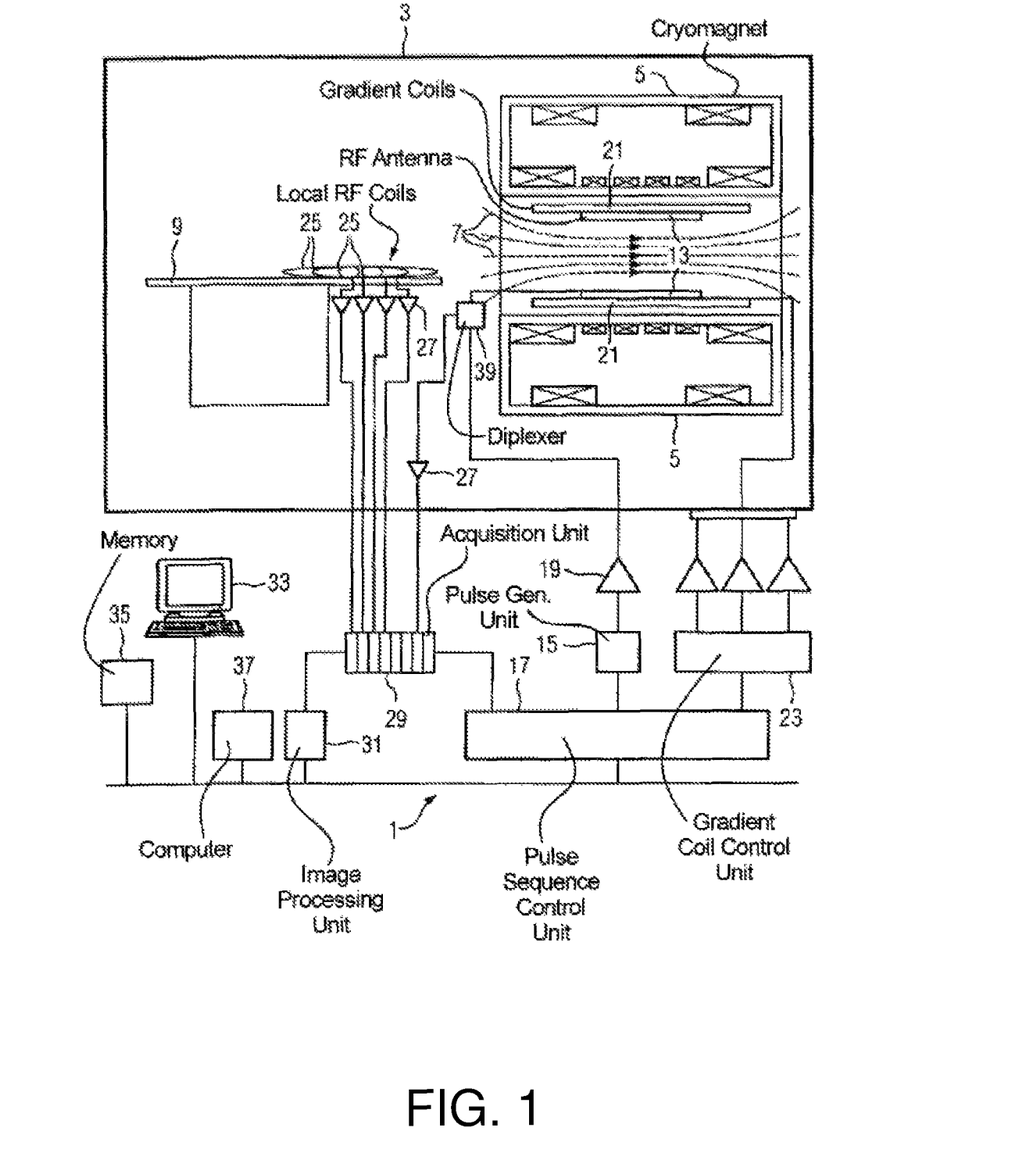
FIG. 1 schematically illustrates the basic components of a MM system constructed and operating in accordance with embodiments of the present disclosure.

FIG. 1 schematically shows the design of a magnetic resonance (MR) system 1 with certain components in accordance with embodiments of the present disclosure. The MR system 1 is configured, inter alia, to provide various magnetic fields tuned to one another as precisely as possible in terms of their temporal and spatial characteristics to facilitate examination of portions of a subject's body using MM techniques.

A strong magnet 5 (typically a cryomagnet) having a tunnel-shaped opening is provided in a RF-shielded measurement chamber 3 to generate a static, strong main (or polarizing) magnetic field, B0, denoted at 7. The strength of the main magnetic field 7 is typically between 1 Tesla and 7 Tesla, although lower or higher field strengths can be provided in certain embodiments. A body or a body part to be examined (not shown) can be positioned within the substantially homogeneous region of the base magnetic field 7, e.g., provided on a patient bed 9.

Excitation of nuclear spins of certain atoms within the body can be provided via RF magnetic field excitation pulses that are radiated using an RF antenna 13, such as a body MR coil. Other configurations of RF coils or antennas can also be provided in further embodiments, and such configurations may be adapted for particular portions of the subject anatomy to be imaged. The RF excitation pulses are generated by a pulse generation unit 15 that is controlled by a pulse sequence control unit 17. After an amplification by a RF amplifier 19, the RF pulses are relayed to the RF antenna 13. The exemplary RF system shown in FIG. 1 is a schematic illustration, and particular configurations of the various components may vary from that illustrated in exemplary embodiments of the disclosure. For example, the MR system 1 can include a plurality of pulse generation units 15, a plurality of RF amplifiers 19, and/or a plurality of RF antennas 13 that may have different configurations depending on the body parts being imaged.

The MR system 1 further includes gradient coils 21 that can provide directionally and temporally varied magnetic gradient fields for spatially selective excitation and spatial encoding of the RF MR signals that are emitted and/or received by the RF antenna(s) 13. The gradient coils 21 are typically oriented along the three primary axes (x- y- and z-directions, where the z-direction is parallel to B0 by convention), although other or additional orientations may be used in certain embodiments. Pulsed current supplied to the gradient coils 21 can be controlled by a gradient coil control unit 23 that, like the pulse generation unit 15, is connected with the pulse sequence control unit 27. By controlling the pulsed current supplied to the gradient coils 21, transient gradient magnetic fields in the x-, y-, and z-directions can be superimposed on the static field B0. This makes it possible to set and vary, for example, the directions and magnitudes of a slice gradient magnetic field Gs, a phase encode gradient magnetic field Ge, and a read (frequency encode) gradient magnetic field Gr, which can be synchronized with emission and detection of the RF pulses. Such combinations of RF pulses and transient magnetic fields can provide spatially selective excitation and spatial encoding of RF signals.

RF signals emitted by the excited nuclear spins can be detected by the RF antenna 13 and/or by local coils 25, amplified by associated RF preamplifiers 27, and processed further and digitized by an acquisition unit 29. In certain embodiments where a coil 13 (such as, for example, a body coil) can be operated both in transmission mode and in acquisition mode (e.g., it can be used to both emit RF excitation pulses and receive RF signals emitted by nuclear spins), the correct relaying of RF energy is regulated by an upstream transmission-reception diplexer 39.

An image processing unit 31 can generate one or more images based on the RF signals that represent image data. Such images can be presented to a user via an operator console 33 and/or be stored in a memory unit 35. The operator console can include, e.g., one or more display devices and input devices such as, e.g., a keyboard, a mouse, a touchscreen, etc. A processor arrangement 37 can be provided in communication with the memory unit 35, and configured to execute computer-executable instructions stored in the memory unit 35 to control various individual system components. For example, the processor arrangement 37 can be configured by programmed instructions to control components such as, e.g., the gradient coil control unit 23, the pulse generation unit 15, and/or the pulse sequence control unit 27 to generate particular sequences of RF pulses and magnetic field variations, process and/or manipulate image data, etc., according to exemplary embodiments of the disclosure described herein.

Embodiments of the present disclosure can provide an MRI system 1, such as that shown in FIG. 1, which is configured to provide MRI sequences of gradient and RF pulses and display generated images in substantially real time for improved MRI guidance of certain procedures such as interventions and electrode placements. The image data obtained in accordance with embodiments of the present disclosure uses compressed sensing concepts, and takes advantage of both the temporal nature of the procedure and qualitative differences in the signal changes in the planned needle path/trajectory and in regions away from this path, as described in detail below.

The MR system 1 can be configured to process the resulting image data to generate high-resolution images with in-plane spatial resolution of about 0.5-2 mm in the region that includes the needle or instrument path. In certain embodiments, higher or lower spatial resolutions may be generated, e.g., based on the such factors as the desired precision of the insertion procedure, the size and/or shape of the needle or other inserted object, the size and location of the target site, etc. Such images can be generated effectively in real time, e.g., at frame rates of about 0.5 to 15 frames per second (fps), thereby avoiding the need to interrupt the insertion procedure to obtain slower verification images. In further embodiments, higher or lower frame rates may be used, e.g., based on such factors as the duration of the insertion procedure and desired rate of insertion.

Trajectory Determination

Prior to beginning the actual insertion or placement procedure, a needle trajectory can be determined using, e.g., any appropriate high-resolution MRI technique including but not limited to TSE, GRE and true-FISP sequences, to generate a "planning" image of the region of the subject that contains the internal target site. Image data acquisition time is not critical for the planning image because this image is obtained performed prior to the actual time-dependent insertion or placement procedure. The spatial trajectory or path for the insertion procedure can be determined from the planning image, e.g., by selecting an insertion point and identifying the target site, such that the needle trajectory will lie along a substantially straight line connecting these two points.

The planning image data can be obtained with the MRI system 1, stored in memory arrangement 33, and displayed on the operator console 33. The trajectory can then be determined interactively by a user, e.g., by viewing and manipulating the displayed image of the region that includes the planned trajectory, and using any appropriate input method to identify the endpoints of the path (e.g. the insertion point and the target site). The MRI system 1 (e.g., the computer 37 and image processing unit 31) can be configured to calculate the planned trajectory in three dimensions and store this spatial information in memory arrangement 35. The trajectory information includes, for example, predetermined information about where the needle should appear in the imaged region of the subject during the procedure, in which direction it is most likely to be advanced (based on the operator substantially following the desired trajectory), and the maximum penetration depth (e.g., a depth corresponding approximately to the depth of the predetermined target site).

Needle/Object Imaging

Needles or other medical devices used in MRI-guided procedures are typically made of metal. Such objects typically generate artifacts in MRI images. For example, magnetization of a needle can produce a local signal drop in the MR image data resulting from a mismatch in magnetic susceptibility between the metallic needle and the surrounding biological tissue. The needle can induce a local field inhomogeneity that affects the coherency of the MR signal, leading to a local loss of signal, or signal "void." This susceptibility artifact can appear as a dark or black region in the image, where the size of the artifact can be larger than the physical size of the needle. The size and shape of the needle artifact is highly dependent on the orientation of the needle with respect to the main magnetic field $B_o$ of the MRI system 1, as well as the particular imaging parameters used such as, e.g., echo time (TE) and bandwidth. Observations and discussions of these effects on artifact appearance are described, e.g., in Lewin et al., *American Journal of Roentgenology*, 166 (6), 1337-1345 (1996), which is incorporated herein by reference in its entirety.

To detect and track the needle during an intervention, it is desirable to predict the appearance of the needle artifact. Although the size and shape of the artifact are dependent on several factors (as described, e.g., in Lewin et al.), the needle artifact typically has the shape of a cylindrical signal void. This void can appear substantially circular in images acquired perpendicular to the needle axis, and as an elongated shape in image slices acquired at an angle to (or parallel to) the needle axis. For a particular MR imaging protocol and set of parameters (e.g. main field strength, echo times, etc.), together with the size/material and approximate orientation of the needle (e.g., substantially along the predetermined trajectory), the expected artifact size and shape can be predicted for various imaging plane orientations using known data. This information can be stored and processed by the MRI system 1, and utilized in the imaging procedures described herein to more accurately track the position of the needle during an intervention or similar procedure.

Figure 2A:
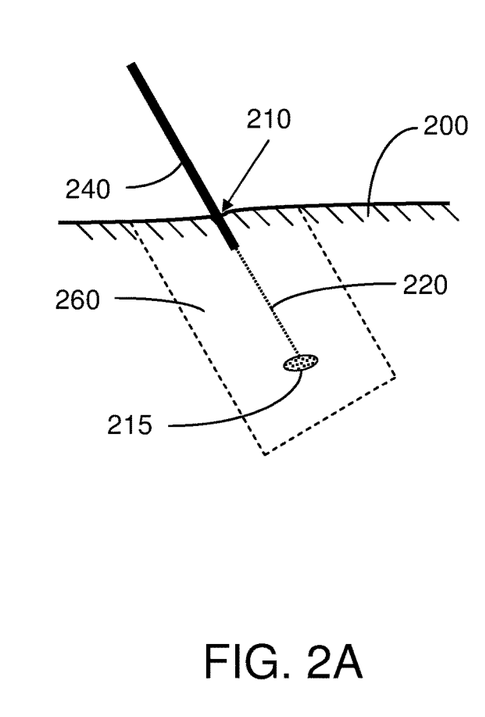
FIGS. 2A and 2B are schematic side-view illustrations of an exemplary insertion procedure of an object along a trajectory toward a target site in a biological tissue, shown at two different stages of the procedure.
Figure 2B:
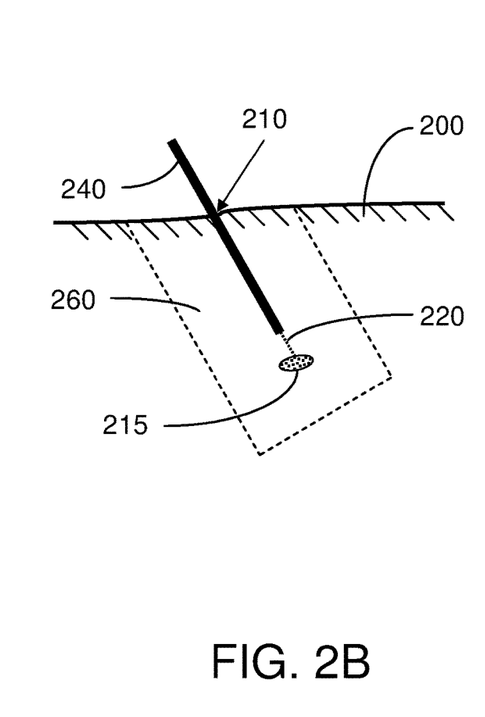

Additionally, the image of the region/volume away from the planned trajectory is unlikely to change if it is imaged within a sufficiently short timeframe, e.g., during an uninterrupted advancement of the needle to a target site. For example, a schematic side view of an intervention procedure is shown at an early time and a later time in FIGS. 2A and 2B, respectively. In these figures, the predetermined trajectory 220 is represented by a dotted line between the starting (insertion) point 210 and the target site 215 that lies within the subject 200. In FIG. 2A, the distal end of the needle 240 within the subject 200 is shown just after being inserted through the starting point 210. FIG. 2B shows this same procedure at a subsequent time, when the distal end of the needle 240 has advanced closer to the target site 215 along the desired trajectory 220.

The dashed line in FIGS. 2A-B defines an approximate region of interest (ROI) 260, i.e., a spatial region close to the predetermined trajectory. The ROI 260 can be, e.g., a substantially cylindrical volume having its axis along the trajectory 220. For example, the ROI can typically encompass or include a volume within a radius of about 1-2 cm around the preplanned trajectory. Other shapes and/or sizes for the ROI 260 can be defined in further embodiments, for example, based on the shape of the needle and characteristics of the subject 200.

Image data for the region of the subject 200 lying outside of the ROI 260 is not expected to change significantly during a relatively short-time guided insertion procedure, e.g., when motion effects can be ignored. Accordingly, image processing time during a guided procedure can be reduced by using obtained image data to generate images primarily of the region of interest 260, as described in more detail below.

Image Acquisition Using Compressed Sensing

Compressed sensing (CS) is a known approach to facilitate reconstruction of a signal using a low sampling rate, e.g. a rate that is below the Nyquist sampling rate. CS techniques are based on the observation that many signals of interest (including MRI imaging signals) may have a sparse representation when using a particular transform. Accordingly, there may exist a particular transform space (a "sparsity space") for a given signal in which most of the transform coefficients are small or zero. Such small coefficients can be assumed to be zero without significant loss of signal quality (the sparseness assumption).

Accordingly, signal reconstruction can often be well-approximated by determining only the limited set of large transform coefficients in the sparsity space. This reduction in the amount of coefficients needed to reproduce the MM signal can facilitate much faster imaging times than conventional reconstructions that use the entire spectrum of coefficients associated with other (non-sparse) transform spaces. An overview of using CS techniques to reconstruct MRI signals and generate images therefrom is provided, e.g., in M. Lustig et al., *IEEE Sig. Proc. Mag.* (March 2008), pp. 72-82, which is incorporated herein by reference in its entirety.

CS-based MRI data processing times can be reduced further by reconstructing image data primarily for the region of interest 260, which contains the advancing needle 240 or other object to be tracked during an MRI-guided procedure. Such reconstruction of a portion of the image can be performed, e.g., using a "mask"-based approach as described, e.g., in U.S. Patent Publication No. 2013/0114872 of Chen et al., the disclosure of which is incorporated herein by reference in its entirety. Other known techniques for reconstructing only a portion of an MR image from image data can be used in further embodiments.

To decrease potential artifacts, undersampled images at different time points can be combined to one joint image, thereby reducing the effective degree of undersampling when displaying or analyzing the image.

Embodiments of the present disclosure can use CS techniques for rapid imaging during a guided procedure that take advantage of these aspects of an intervention or similar procedure. For example, a compressed sensing cost function $f(x_t)$ can be defined as:

$$f(x_t) = \underbrace{\frac{1}{2}\|Ax_t - y\|_2^2}_{\text{Match measured data}} + \underbrace{\lambda_1 \|x_t - (x_{ref} + \hat{x}_{Needle,t})\|_1}_{\text{Similar to predicted image}} + \underbrace{\lambda_2 \|x_t - x_{t-1}\|_1}_{\text{Similar to previous frame}} \quad (1)$$

In this equation, $x_t$ is the current image being computed at time t, A is the MRI sampling operator, y is the measured (raw) k-space data, $x_{ref}$ represents the predicted image without the presence of needle artifacts $\hat{x}_{Needle,t}$ represents a predicted needle artifact, $x_{t-1}$ is the previous image that was computed at time t-1, and $\lambda_1$ and $\lambda_2$ are weighting coefficients.

As indicated by the labels below equation (1), the first term on the right-hand side represents a difference between the image being estimated, as obtained under a particular Mill sampling operator A, and the raw measured k-space data y; the second term on the right-hand side represents a difference between the estimated image and the separate predicted artifact-free image plus the predicted needle artifact; and the third term on the right-hand side of eq. (1) represents a change of the estimated image from the previous calculated image (e.g., the image x that was calculated using this same cost function for the preceding frame at time t-1).

The constants $\lambda_1$ and $\lambda_2$ determine how strongly regularized the reconstruction should be. For example, selecting a large value for $\lambda_1$ and $\lambda_2$ very small or zero (e.g., $\lambda_1$ is of order unity or larger, $\lambda_2$ is approximately 0.1 or less) would result in an estimated image that is very close to the predicted image, because the middle term on the right side of equation (1) is emphasized. Alternatively, setting $\lambda_1$ to a small value (e.g., about 0.1 or less) and selecting a large value for $\lambda_2$ of about 1 or greater would produce images that are slowly updated because the similarity of each image to the previous frame is emphasized in the image generation procedure. In certain embodiments, the weighting coefficients $\lambda_1$ and $\lambda_2$ can each be selected to be close to 1 (e.g., between about 0.5 and 1.5) to provide a balanced effect of using the actual image data, the previous frame data, and the predicted image data when generating each successive image frame. Large values of the weighting coefficients $\lambda_1$ and $\lambda_2$ (e.g., greater than about 2 or 3) may not be desirable, as such weightings of the terms in the compressed sensing cost function $f(x_t)$ may lead to undesirable deviations from the actual measured image data.

The desired image can be determined by minimizing the cost function $f(x_t)$ shown in Eq. (1) using iterative computational techniques known in the art. In this manner, raw MR image data can be used with the above cost function to generate real-time high-resolution images of the ROI around the predetermined trajectory.

The sparsity condition that facilitates CS techniques is not always fulfilled in general MR signals (image data sets). However, in dynamic imaging as described here, data sparsity can readily be introduced by the latter two terms on the right in Eq. (1). For example, the actual calculated image will have a sparse difference when compared to the predicted image, which includes the background image plus the predicted needle artifact. Also, the difference between the calculated image and the previous image obtained in the previous frame (e.g., a very short time interval prior) will also be sparse. In other words, only parts of the overall field of view (e.g., the region of interest around the desired trajectory) change at a high temporal rate (e.g., the needle artifact shifts during advancement of the needle) while other portions of the imaged volume remain stationary or change slowly, and the change between successive images (which is primarily the change in the advancing needle artifact between frames) is also small.

In certain embodiments of the disclosure, a spiral or radial k-space sampling sequence can be used to obtain the image data. The angular projections of such spiral or radial sequence (as compared to, e.g., a Cartesian sampling approach) would be randomly under-sampled. Such under-sampling can result in, for example, a 2-10-fold reduction in image data acquisition time as compared to a comparable fully-sampled sequence.

In other embodiments, a FISP sequence can be used to obtain the image data, e.g., a balanced FISP (True-FISP) technique. For example, the phase-encoding gradient steps in a Cartesian FISP data acquisition would be randomly under-sampled except for a fully-sampled region near the origin of k-space which would be fully sampled. An example of this type of sampling approach is described, e.g., in S. S. Hegde et al., *Magnetic Resonance in Medicine* 2015(2); 74:452-461, which is incorporated herein by reference in its entirety.

Real-Time Image-Guided Procedure

Figure 3:
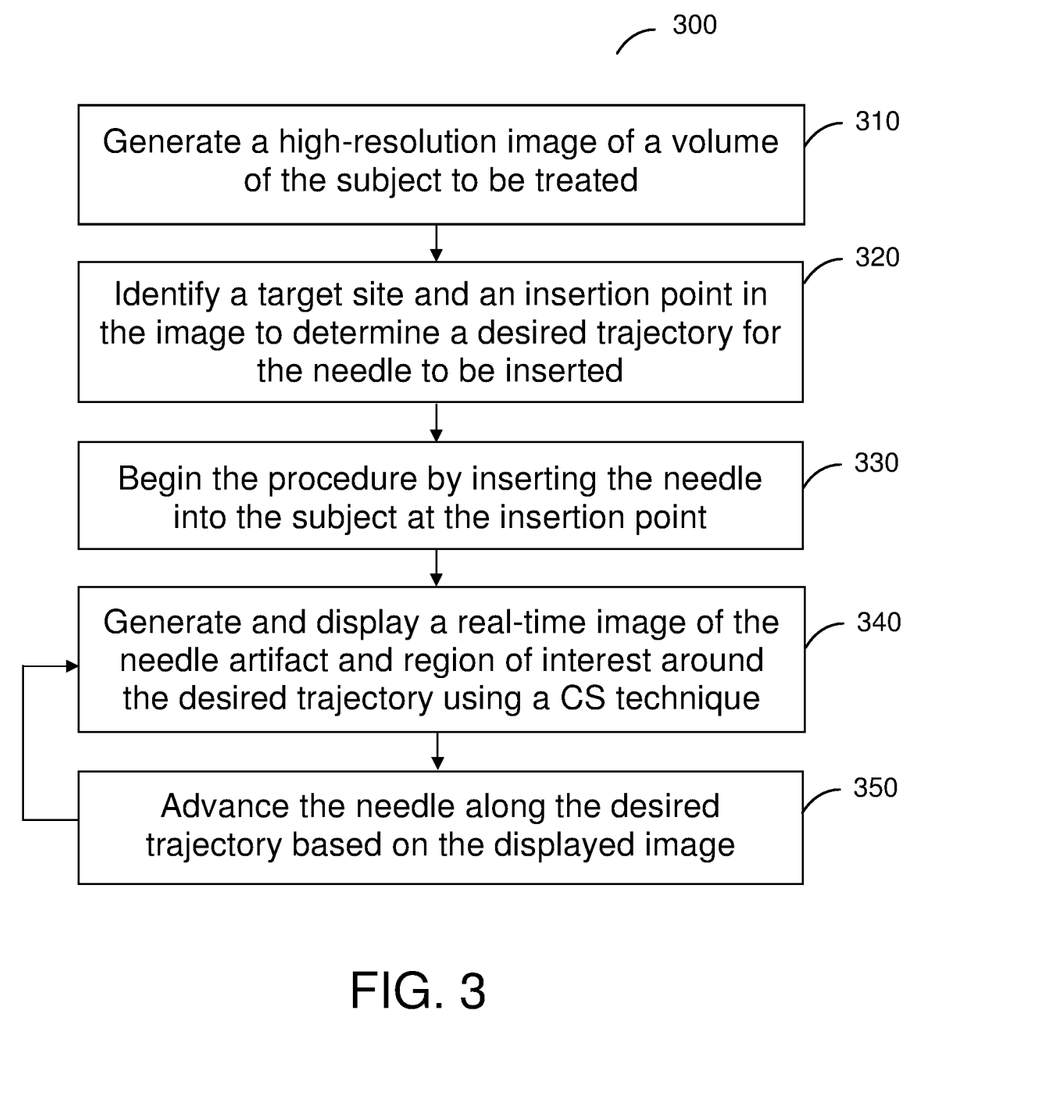
FIG. 3 is a flowchart illustrating an Mill-guided method in accordance with embodiments of the present disclosure.

A flowchart 300 illustrating an exemplary method in accordance with embodiments of the disclosure is shown in FIG. 3. In the initial step 310, a high-resolution "planning" image of the portion of the subject to be treated is generated using any appropriate MRI technique. The image can be displayed (and optionally manipulated) on a user console 33 of the MRI system 1, and the starting/insertion point and target site for the MRI-guided procedure can then be identified on this displayed image by a user using any appropriate input method in step 320. The insertion point and target site can also be used to calculate the set of spatial coordinates describing the desired trajectory. This trajectory is typically a straight line connecting the insertion point and target site, but other path shapes can be used in certain embodiments, e.g., to maneuver around a particular internal location or structure of the subject.

The image-guided procedure is then initiated in step 330 by beginning insertion of the needle (or other object) into the subject at the insertion point. The direction of the needle is preferably aligned with the predetermined trajectory, to the extent possible. At this time, continuous real-time imaging of the subject in the region of the procedure using a compressed sensing technique as described herein is begun in step 340. Images can be obtained rapidly using a compressed sensing technique by minimizing the cost function presented in Eq. (1) based on the raw image data obtained, e.g., from the RF coils 25 and through the acquisition unit 29 of the MRI system 1. The images can be generated using the image processing unit 31 and then displayed on a display connected to the MRI system 1 that is a part of the user console 33 or a separate display device provided in communication with the image processing unit 31. A line or other indicator showing the predetermined trajectory can be generated and superimposed on the MR images of the subject together with the needle artifact that indicates the location of the needle within the subject.

The guided procedure (e.g. an intervention) is then continued by continuing to advance the needle along the predetermined trajectory in step 350. The user can continuously adjust the angle or direction of the needle as it is advanced based on the real-time images, such that the insertion procedure proceeds along the predetermined trajectory. The displayed images can optionally be manipulated by user input such that a plurality of viewing angles can be shown, either simultaneously or sequentially, to facilitate directional adjustments to the needle advancement.

Steps 340 and 350 can be repeated until the needle reaches the target site or the procedure is stopped for some other reason. In this manner, the system s and methods described herein can provide accurate real-time imaging during the guided procedure so the insertion follows the predetermined trajectory to the target site.

The foregoing merely illustrates the principles of the present disclosure. Various modifications and alterations to the described embodiments will be apparent to those skilled in the art in view of the teachings herein. It will thus be appreciated that those skilled in the art will be able to devise numerous techniques which, although not explicitly described herein, embody the principles of the present disclosure and are thus within the spirit and scope of the present disclosure.

What is claimed is:

1. A method for directing an object from a starting point to a target site in a biological tissue using real-time magnetic resonance imaging (MRI) guidance, comprising the steps of:
   generating a high-resolution planning image of a region of the biological tissue that includes the starting point and the target site;
   determining a trajectory from the starting point to the target site using the planning image;
   generating and displaying a series of images of the region of the biological tissue and of an artifact based on the position of the object using a compressed sensing technique, wherein the series of images is generated and displayed substantially in real time;
   wherein each image of the series of images is generated using a compressed sensing technique based on minimization of a cost function that includes:
      a difference between the current image and the corresponding raw image data based on a particular MRI sampling operator;
      a difference between the current image and a sum of a baseline image and a predicted artifact; and
      a difference between the current image and the most recent image.

2. The method of claim 1, further comprising:
   introducing a distal end of the object into the starting point in a direction substantially corresponding to the direction of the trajectory; and
   advancing the object further into the biological tissue along the trajectory toward the target site, wherein a direction of the advancement is based on the displayed series of images.

3. The method of claim 1, wherein the cost function is denoted as $f(x_t)$ and has the form:

$$f(x_t) = \frac{1}{2}\|Ax_t - y\|_2^2 + \lambda_1 \|x_t - (x_{ref} + \hat{x}_{Needle,t})\|_1 + \lambda_2 \|x_t - x_{t-1}\|_1$$

wherein $x_t$ represents the current image being computed at time t, A represents an MRI sampling operator, y represents measured (raw) k-space data, $X_{ref}$ represents a predicted image without the presence of needle artifacts, $\hat{x}_{Needle,t}$ represents a predicted needle artifact, $x_{t-1}$ represents the previous image that was computed at time t-1, and $\lambda_1$ and $\lambda_2$ are weighting coefficients.

4. The method of claim 3, wherein a value for $\lambda_1$ is between 0.5 and 1.5.

5. The method of claim 3, wherein a value for $\lambda_2$ is between 0.5 and 1.5.

6. The method of claim 1, wherein each image of the series of images includes a representation of the trajectory.

7. The method of claim 1, wherein the series of images is generated at a rate that is between 0.5 and 15 images per second.

8. The method of claim 1, wherein each image of the series of images has an in-plane resolution that is between 0.5 mm and 2 mm.

9. The method of claim 1, wherein each image of the series of images is generated using a radial sampling trajectory in k-space.

10. The method of claim 1, wherein each image of the series of images is generated using a spiral sampling trajectory in k-space.

11. The method of claim 1, wherein each image of the series of images is generated using a steady-state free precession technique.

12. The method of claim 1, wherein each image of the series of images is generated using a balanced steady-state free precession technique.

13. An MRI system configured to facilitate directing an object from a starting point to a target site in a biological tissue using real-time magnetic resonance imaging (MRI) guidance, comprising:
    a radio frequency (RF) signal generator and a magnetic field gradient generator which are together configured to provide an imaging protocol comprising a plurality of imaging pulse sequences that further comprise a plurality of RF pulse sequences and magnetic field gradient sequences for acquisition of image data; and
    an image processing unit configured to generate a series of images based on the image data,
wherein the MRI system is configured to:
    generate a high-resolution planning image of a region of the biological tissue that includes the starting point and the target site;
    determine a trajectory from the starting point to the target site based on the planning image; and
    generate and display the series of images of the region of the biological tissue and of an artifact using a compressed sensing technique, wherein each image is based on a current position of the object, and wherein the series of images is generated and displayed substantially in real time;
wherein each image of the series of images is generated using a compressed sensing technique based on minimization of a cost function that includes:
    a difference between the current image and the corresponding raw image data based on a particular MRI sampling operator;
    a difference between the current image and a sum of a baseline image and a predicted artifact; and
    a difference between the current image and the most recent image.

14. The system of claim 13, wherein the cost function is denoted as $f(x_t)$ and has the form:

$$f(x_t) = \frac{1}{2}\|Ax_t - y\|_2^2 + \lambda_1 \|x_t - (x_{ref} + \hat{x}_{Needle,t})\|_1 + \lambda_2 \|x_t - x_{t-1}\|_1$$

wherein $x_t$ represents the current image being computed at time t, A represents an MRI sampling operator, y represents measured (raw) k-space data, $x_{ref}$ represents a predicted image without the presence of needle artifacts, $\hat{x}_{Needle,t}$ represents a predicted needle artifact, $x_{t-1}$ represents the previous image that was computed at time t-1, and $\lambda_1$ and $\lambda_2$ are weighting coefficients.

15. The system of claim 14, wherein at least one of $\lambda_1$ and $\lambda_2$ has a value that is between 0.5 and 1.5.

16. The system of claim 13, wherein each image of the series of images includes a representation of the trajectory.

17. The system of claim 13, wherein the system is configured to generate the series of images at a rate that is between 0.5 and 15 images per second.

18. The system of claim 13, wherein the system is configured to generate each image of the series of images with an in-plane resolution that is between 0.5 mm and 2 mm.

19. The system of claim 13, wherein the system is configured to generate each image of the series of images using at least one of a spiral sampling trajectory or a radial sampling trajectory in k-space.

20. The system of claim 13, wherein the system is configured to generate each image of the series of images using a steady-state free precession technique.

* * * * *